(12) United States Patent
Meyer-Pittroff (10) Patent No.: US 9,175,199 B2
(45) Date of Patent: Nov. 3, 2015

(54) METHOD FOR PROVIDING AND USING AN ALCOHOL AND USE OF THE ALCOHOL FOR INCREASING THE EFFICIENCY AND PERFORMANCE OF AN INTERNAL COMBUSTION ENGINE

(75) Inventor: Roland Meyer-Pittroff, Frelsing (DE)

(73) Assignee: SILICON FIRE AG, Meggen (CH)

( * ) Notice: Subject to any disclaimer, the term of this patent is extended or adjusted under 35 U.S.C. 154(b) by 32 days.

(21) Appl. No.: 13/878,201

(22) PCT Filed: Oct. 4, 2011

(86) PCT No.: PCT/EP2011/067315
§ 371 (c)(1),
(2), (4) Date: Jun. 28, 2013

(87) PCT Pub. No.: WO2012/045743
PCT Pub. Date: Apr. 12, 2012

(65) Prior Publication Data
US 2013/0284138 A1    Oct. 31, 2013

(30) Foreign Application Priority Data

Oct. 6, 2010  (EP) .................. PCT/EP2010/064948
Feb. 1, 2011  (EP) ..................................... 11152947
Feb. 22, 2011 (EP) ..................................... 11155310

(51) Int. Cl.
*F02B 43/00*   (2006.01)
*C09K 5/04*    (2006.01)
*B01J 19/00*   (2006.01)
*C07C 29/152*  (2006.01)
(Continued)

(52) U.S. Cl.
CPC ............... *C09K 5/04* (2013.01); *B01J 19/0093* (2013.01); *C07C 29/152* (2013.01);
(Continued)

(58) Field of Classification Search
CPC .............. F02B 1/04; F02B 43/10; F02B 3/06; F02M 25/00; F02D 19/08
USPC ........................................................ 123/1 A
See application file for complete search history.

(56) References Cited

U.S. PATENT DOCUMENTS 4,776,171 A    10/1988  Perry, Jr. et al.
6,302,929 B1 *  10/2001  Gunnerman .................... 44/302
(Continued)

FOREIGN PATENT DOCUMENTS

DE    2639187 A1   3/1978
EP    0539244 A1   4/1993
(Continued)

OTHER PUBLICATIONS

Bayraktar et al; "An experimental study on the performance parameters of an experimental CI engine fueled with diesel-methanol-dodecanol blends".; Fuel. IPC Science and Technology Press. Guildford. GB; vol. 87. No. 2; Nov. 15, 2007. pp. 158-164; XP022346675.

(Continued)

*Primary Examiner* — Lindsay Low
*Assistant Examiner* — Charles Brauch
(74) *Attorney, Agent, or Firm* — Sideman & Bancroft LLP; Guy W. Chambers (57) ABSTRACT

A method for providing and consuming a storable and transportable, alcohol-containing cooling fluid comprising the following steps:
- providing a gas with carbon dioxide fraction as a carbon supplier;
- providing a hydrogen fraction;
- producing a gaseous starting material by mixing the carbon dioxide fraction and hydrogen fraction;
- passing of the starting material through a reactor with a catalyst to synthesize a cooling fluid mixture of alcohol and water; and
- using the cooling mixture for cooling intake air, and/or compressor air or/and a fuel-air mixture of an internal combustion engine by evaporating the cooling fluid.

14 Claims, 8 Drawing Sheets

(51) Int. Cl.
*F02M 27/02* (2006.01)
*F02M 25/028* (2006.01)
*F02M 25/022* (2006.01)
*F02D 19/06* (2006.01)
*F02B 3/06* (2006.01)
*F02M 25/00* (2006.01)
*F02B 1/04* (2006.01)
*F02D 19/08* (2006.01)
*F02B 43/10* (2006.01)

(52) U.S. Cl.
CPC ....... *F02D 19/0655* (2013.01); *F02D 19/0671* (2013.01); *F02M 25/028* (2013.01); *F02M 25/0228* (2013.01); *F02M 27/02* (2013.01); *B01J 2219/00835* (2013.01); *B01J 2219/00869* (2013.01); *B01J 2219/00871* (2013.01); *C10G 2300/4043* (2013.01); *C10G 2300/4068* (2013.01); *F02B 1/04* (2013.01); *F02B 3/06* (2013.01); *F02B 43/10* (2013.01); *F02D 19/08* (2013.01); *F02M 25/00* (2013.01); *Y02E 60/364* (2013.01); *Y02T 10/121* (2013.01); *Y02T 10/36* (2013.01)

(56) References Cited

U.S. PATENT DOCUMENTS

| | | | |
|---|---|---|---|
| 6,321,145 B1 * | 11/2001 | Rajashekara | 701/22 |
| 6,405,720 B1 * | 6/2002 | Collier, Jr. | 123/568.12 |
| 2003/0065042 A1 * | 4/2003 | Shaw | 518/702 |
| 2008/0058434 A1 * | 3/2008 | Tonkovich et al. | 518/704 |

FOREIGN PATENT DOCUMENTS

JP 07253025 A 10/1995
WO WO 2007/002371 A2 1/2007

OTHER PUBLICATIONS

International Search Report under Patent Cooperation Treaty (PCT) for PCT/EP2011/067315; dated Feb. 17, 2012; 4 pages.
International Preliminary Report of Patentability under Patent Cooperation Treaty (PCT) for PCT/EP2011/067315; dated Apr. 9, 2013; 7 pages.

* cited by examiner

METHOD FOR PROVIDING AND USING AN ALCOHOL AND USE OF THE ALCOHOL FOR INCREASING THE EFFICIENCY AND PERFORMANCE OF AN INTERNAL COMBUSTION ENGINE

FIELD OF THE INVENTION

The present invention relates to a method for providing and using an alcohol. Furthermore, it concerns the use of the alcohol for increasing the efficiency and performance of an internal combustion engine, e.g. a diesel engine. Methanol mixtures are concerned in particular.

CROSS-REFERENCES TO RELATED APPLICATIONS

The present application claims the priority of the Patent Cooperation Treaty Application No. PCT/EP2011/067315, which was filed on 4 Oct. 2011 under the title "A METHOD FOR PROVIDING AND USING AN ALCOHOL AND USE OF THE ALCOHOL FOR INCREASING THE EFFICIENCY AND PERFORMANCE OF AN INTERNAL COMBUSTION ENGINE".

The present application claims the priority of the international patent application PCT/EP2010/064948, which was filed on 6 Oct. 2010 under the title "METHOD AND INSTALLATION FOR SYNTHESISING HYDROCARBON".

The present application also claims the priority of the provisional European patent application EP11152947.5, which was filed on 1 Feb. 2011 under the title "METHOD FOR PROVIDING AND USING AN ALCOHOL AND USE OF THE ALCOHOL FOR INCREASING THE EFFICIENCY AND PERFORMANCE OF AN INTERNAL COMBUSTION ENGINE".

The present application also claims the priority of the European patent application EP11155310.3, which was filed on 22 Feb. 2011 under the title "METHOD FOR PROVIDING AND USING AN ALCOHOL AND USE OF THE ALCOHOL FOR INCREASING THE EFFICIENCY AND PERFORMANCE OF AN INTERNAL COMBUSTION ENGINE".

All of the preceding applications are incorporated herein by reference in all their entirety for all purposes.

BACKGROUND OF THE INVENTION

Carbon dioxide $CO_2$ is a chemical compound of carbon and oxygen. Carbon dioxide is a colorless and odorless gas. It is a natural component of air with low concentration and is produced in living beings in cellular respiration, but also during the combustion of carbonaceous substances under sufficient presence of oxygen. Since the beginning of industrialization, the $CO_2$ fraction in the atmosphere has been rising considerably. The main cause for this rise are the (so-called anthropogenic) $CO_2$ emissions produced by humans. The carbon dioxide in the atmosphere absorbs a part of the thermal radiation. This property makes carbon dioxide a so-called greenhouse gas (GHG) and a contributor to the global greenhouse effect.

For this and also other reasons, research and development is carried out in a large number of directions in order to find a way to reduce anthropogenic $CO_2$ emissions. There is strong need for reducing the $CO_2$ emissions, especially in connection with power generation which frequently occurs by incinerating fossil fuels such as coal, oil or gas, but also in connection with other combustion processes such as the incineration of waste. More than 20 billion tons of $CO_2$ are emitted into the atmosphere by such processes per year.

It is seen as a problem that $CO_2$ is produced in the combustion of fossil fuels. Furthermore, finite fossil resources are irrevocably consumed. Mobility in particular leads to larger emissions. That is why research is conducted in a large number of directions in order to reduce the consumption of vehicles or to develop vehicles which are driven completely by regenerative forms of energy.

It is known that the intake air or the fuel-air mixture can be cooled prior to the compression in the intake passage of an internal combustion engine. This leads to an increase in the density of the gas and therefore to an increase in the mass flow through the machine and to the possibility to combust more fuel in the increased air mass, and therefore to an increase in the specific power.

The working process and therefore also the combustion in the combustion chamber of an internal combustion engine commences at a lower temperature. In the case of a predetermined (due to the thermal loading) combustion end temperature (especially in the case of gas turbines due to blade strength), more heat can also be supplied at the start of combustion at lower temperature, which again leads to an increase in the specific power.

It is the state of the art in nearly all modern diesel engines and in many gasoline engines to provide pre-compression of the combustion air or the fuel-air mixture before the combustion chamber with a special compressor (which is also known as a supercharger or compressor) for the reasons as mentioned above. A radial flow compressor is conventionally used for this purpose, which is driven by a radial exhaust-gas turbine (also known as exhaust-gas turbocharger). The radial flow compressor and the radial exhaust-gas turbine are arranged on a common shaft. The gas (or the charge air respectively) will be heated in a polytropic manner as a result of this compression and will be cooled back according to the state of the art by a heat exchanger (also known as an intermediate cooler or intercooler) which is cooled by external air for example in order to increase the power and efficiency of the engine.

The higher specific power of the machine, in combination with losses that remain the same otherwise, additionally leads to an increase in the efficiency, which will be utilized in combustion engines for example by reducing the size of the machine (downsizing).

The intermediate cooler causes additional constructional effort with respective costs and need for space, and also losses concerning power and efficiency due to its flow resistance (pressure losses).

It is also known that by injecting water or a water-alcohol mixture the intake air or the fuel-air mixture of an engine can be cooled, which occurs both before the compression in the intake passage and also after the pre-compression instead of the intermediate cooler, or even after the intermediate cooler. By injecting such a fluid into the intake air or the fuel-air mixture, it is possible to achieve gains in power and efficiency without pressure losses. This is caused by the fact that the water or the water-alcohol mixture will evaporate and will cool the intake air or the fuel-air mixture according to its evaporation heat.

If this fluid is combustible, which occurs in a water-alcohol mixture, it takes part in the subsequent combustion process in the internal combustion engine under delivery of additional mechanical power.

Different effects can be achieved depending on the configuration of the respective units of such an internal combustion engine and depending on the use of water or water-alcohol mixtures. As a result, the total power and the inner cooling of the internal combustion engine can be increased. This allows downsizing of the internal combustion engine for example, which can contribute to the reduction in the losses and also to a reduction in the emissions.

If alcohol is used, then such alcohol will combust together with the fuel (primary fuel) in the internal combustion engine. If the alcohol were obtained from fossil raw materials, the combustion of the alcohol would lead to additional $CO_2$ emissions however.

It is therefore examined whether or not and the extent to which alcohol can be produced from biogenic resources and can be used in vehicle engines. The use of $CO_2$-neutral alcohol would reduce the $CO_2$ emissions of the vehicle engine which have an effect on the climate. The main focus in this application is on methanol, ethanol and butanol. It has regretfully been noticed that the production of $CO_2$-neutral alcohol entails numerous other disadvantages. The production of these alcohols is frequently in direct competition with food production, or the costs for the $CO_2$-neutral alcohol are considerably higher than the costs of fossil fuels.

Other alternative alcohol-based fuels are often more expensive than the fossil fuels. This is partly caused by the fact that all costs including the environmental costs are included in the production of $CO_2$-neutral alcohol, whereas fossil fuels are currently still offered without the actual consideration of the so-called external costs.

Methanol is an especially advantageous alcohol because it is the simplest alcohol that is available. Methanol is mostly produced until now from fossil raw materials such as natural gas for example. Numerous methods and reactors for the production of methanol are known. Respective exemplary patent applications and patents are mentioned below:

EP 0 790 226 B1;
WO 2010/037441 A1;
EP 4 483 919 A2.

For the initially mentioned applications there is a demand for the provision of an alcohol-water mixture, which on the one hand is suitable as a cooling fluid and on the other hand is $CO_2$-neutral and cheap in production. Moreover, the alcohol shall not be in competition with food production.

BRIEF SUMMARY OF THE INVENTION

It is now the object of developing a respective method for providing an alcohol-containing cooling fluid which is useful from an ecological and economical standpoint. The cooling fluid shall be optimally suitable for cooling the intake air or the fuel-air mixture of an internal combustion engine (e.g. a car or ship engine).

A new process chain of the present invention deals with the provision and consumption of a storable and transportable alcohol-containing cooling fluid. The preferred method comprises the following steps:

providing a gas with a carbon dioxide fraction ($CO_2$) as a carbon supplier;
providing a hydrogen fraction ($H_2$);
providing a starting material which comprises the carbon dioxide fraction and the hydrogen fraction;
introduction of the starting material into a reactor;
passage of the starting material through a reaction section of the reactor which is equipped at least partly with a catalyst in order to synthesize the alcohol-containing cooling fluid in a catalytic synthesis process;
providing the alcohol-containing cooling fluid at an output end of the reactor, wherein said cooling fluid is a mixture of an alcohol fraction and a water fraction;
using said alcohol-containing cooling fluid in an internal combustion engine which is supplied with air or a fuel-air mixture, wherein the air or fuel-air mixture is (pre-) cooled by evaporation of the alcohol-containing cooling fluid.

This especially concerns heat engines with internal combustion, which means internal combustion engines which aspirate the air or the fuel-air mixture in a gaseous manner, compress the same and supply heat to said working medium after compression by combustion within the working medium. Such internal combustion engines are gasoline engines and diesel engines and open gas turbines. The invention can therefore preferably be applied to gasoline engines, diesel engines and open gas turbines.

The invention is intentionally using carbon dioxide and hydrogen as the starting materials because the carbon dioxide can be "recycled" in this manner and can be used as a carbon supplier. If the hydrogen is generated from regenerative energy and the carbon dioxide is obtained from exhaust gases or biomass, the alcohol-containing fluid which is synthesized catalytically from these starting materials is regarded as being $CO_2$-neutral. Furthermore, this procedure offers the advantage that it supplies a methanol-water mixture in the synthesis of methanol for example which is directly suitable for intake cooling or intermediate cooling. The composition of the alcohol-containing fluid is ideal from a chemical-physical point of view in order to be used as a fluid intake cooling or intermediate cooling, and is characterized in that it also offers advantages from an environmental point of view.

Especially where the intermediate cooling of the diesel engines is concerned, a mixed operation in which diesel fuel on the one hand and pure alcohol is used as a cooling fluid on the other hand (which acts like petrol during combustion) could negatively affect the operational lifespan of the diesel engine. That is why the use of a cooling fluid is advantageous especially in these cases, which cooling fluid consists of up to two-thirds of water apart from the remainder of methanol.

Other than in previous methanol production processes, the product of the methanol synthesis process which consists of methanol and water can be regarded and used directly as a cooling fluid. No energy input is required for distilling the product of the synthesis process. The energy input for distilling, which is typically performed for obtaining pure alcohol, leads to an increase in the price of the alcohol. In accordance with the invention, the directly produced alcohol-water mixture is used for intermediate cooling or intake cooling, which is provided by the catalytic synthesis of carbon dioxide and hydrogen.

The method differs from the state of the art among other things in such a way that no fossil raw materials such as methane gas are used in order to produce the alcohol. Furthermore, the method in accordance with the invention uses catalytic synthesis of carbon dioxide and hydrogen instead of carbon monoxide and hydrogen. The catalytic synthesis of carbon dioxide and hydrogen already supplies a virtually ideal composition of the product as a cooling fluid, as already described above. The direct product of the catalytic synthesis, which will be referred to below as the alcohol-containing cooling fluid, will be used for intake cooling or intermediate cooling.

In accordance with the invention, $H_2$- and $CO_2$-containing synthesis gas is converted in an efficient and economically viable manner into alcohol-containing cooling fluid such as methanol and/or ethanol mixtures.

In accordance with the invention, carbon dioxide is used as the carbon supplier. The carbon dioxide will be made to react with the hydrogen fraction in the presence of a catalyst in order to convert these gases into a cooling fluid, preferably a water-alcohol mixture, and especially preferably a methanol-water mixture.

Preferably, carbon dioxide is taken from a combustion process or an oxidation process of carbon or hydrocarbons by means of $CO_2$ separation. $CO_2$ can be provided by a pipeline or in gas cylinders or tanks. It is also possible to use carbon dioxide from a vehicle such as a ship for example.

The hydrogen can be provided via a pipeline or also in gas cylinders or tanks. Preferably, the hydrogen is produced on site by means of electrolysis of water. Alternatively, the hydrogen could also be produced by a reduction reaction of water with silicon or any other elementary metal.

Carbon dioxide as the carbon supplier can also be taken in accordance with the invention from raw natural gas, which depending on the natural gas source can have a carbon dioxide fraction of over 10%. Carbon dioxide can also originate from industrial processes such as lime burning or calcination into soda.

The method in accordance with the invention for providing the cooling fluid will be controlled and the individual processes will be "linked" with each other in such a way that
- the total yield and the quality of the cooling fluid is ideal for the intended purpose;
- and/or the $CO_2$ (total) emissions will be as minimal as possible;
- and/or the most constant and long-term utilization of the installation will be achieved;
- and/or the product-specific investment and operating costs are kept to the lowest possible level.

Regenerative electrical power is preferably used for providing the cooling fluid.

A methanol-water mixture is preferably produced with a respective installation as a storable and transportable cooling fluid. This means the regenerative energies are converted chemically into a non-critical cooling fluid that can be stored and transported in a relatively simple way.

The production of the cooling fluid as a mixture that can be stored and transported in a relatively simple way can be run down or even interrupted at any time. The parts of the process installation for producing the mixture can be run down or switched off in a relatively simple and rapid way, or they can be operated depending on the network frequency. The decision-making power lies in the field of responsibility of the operator of the installation. This leads to the possibility of allowing the installation to contribute to the stabilization and/or frequency control of the electric interconnected grid.

Preferred embodiments of the invention are based on the production of hydrogen with the help of electrical power which is produced as far as possible in a regenerative way and originates from wind power plants, hydroelectric power plants, geothermal power plants and/or solar power plants. Hydrogen which is produced on site by means of electrolysis or by using elementary silicon or other metals need not be stored or highly compressed or liquefied cryogenically and transported over longer distances, but will be used as an intermediate product which is supplied preferably at the location of its production directly or immediately to the aforementioned reaction for producing the cooling fluid.

An energy-converting process in which regenerative energy is converted into electrical power is followed for example by material-converting (chemical) processes depending on the embodiment of the invention, which is the intermediate provision of hydrogen and the conversion of the hydrogen together with the carbon dioxide into the alcohol-containing cooling fluid, preferably a cooling fluid which contains methanol.

The respective alcohol-water mixture can also be produced according to the invention by using an intelligent energy mix (as described for example in the international patent application WO2010069622 A1) from fossil and regenerative energy.

A new energy-relevant method and a respective use are provided in accordance with the invention by taking into account respective power-related, installation-related and economic requirements in combination with the demand for careful use of all material, energy and economic resources.

It is seen as an advantage of the invention that the reduction in the mean combustion temperature of an internal combustion engine will lead to a reduction in the nitrogen oxide (NOx) emissions.

It is also an advantage of the invention that cooling of the working medium during the compression leads to an increase in the specific power and efficiency of the internal combustion engine.

With regard to the apparatus/construction, the cooling during the compression is realized best by means of a multi-stage compression, e.g. in the case of a two-stage compression of the working medium of the internal combustion engine by a supercharger/compressor and piston in the cylinder or in the case of gas turbines with a low-pressure and high-pressure compressor. Cooling between the individual compression stages, which shall be referred to here as intermediate cooling, can also lead to the aforementioned advantages in addition to the reduction in the compression work, which are caused by an increase in the density of the working medium in the following stages and the reduction in the temperature of the start of the combustion. This leads to increases in the power and efficiency and to a reduction in the NOx emissions.

In accordance with the invention, a carbon dioxide gas is used as a carbon supplier for the production of the alcohol-containing cooling fluid.

In accordance with the invention, a gaseous starting material is provided which comprises carbon dioxide gas and hydrogen gas. In order to ensure that said gaseous starting material is as homogeneous as possible it will be
- mixed in a gas mixture with correct stoichiometric mixture ratio before it is introduced into the reactor, and/or
- it will be evenly divided among the individual reactor tubes of the reactor by using a ring line which is provided upstream of the reactor.

Alternatively, the starting material
- will be mixed in a gas mixture with correct stoichiometric mixture ratio before it is introduced into the reactor, and
- it will be evenly distributed among the individual reactor tubes of the reactor by using a pre-chamber which is connected upstream of the reactor. The pre-chamber is used as a buffer or collector and prevents the formation of strands in the gas flow entering the reactor.

The even distribution of the starting material on entering and flowing through the individual reactor tubes of the reactor is important.

Preferably, the reactor of the invention comprises in all embodiments several reactor elements arranged in a bundled manner, with each of the reactor elements comprising two or three reactor tubes extending parallel with respect to each other. These reactor tubes are connected with each other by deflection elements and produce in their entirety a folded reactor line. This form of arrangement is especially advantageous because it enables a small and compact configuration which can be used in transportable applications or in ships for example.

The invention therefore relates to the cooling of a working medium, i.e. it deals specifically with methods and apparatuses for intake cooling and intermediate cooling of an internal combustion engine.

Further advantageous embodiments are shown in the description, the drawings and the dependent claims.

BRIEF DESCRIPTION OF THE DRAWINGS

The drawings schematically show various aspects of the invention.

DETAILED DESCRIPTION OF THE INVENTON

The term of cooling fluid shall be used here for fluid mixtures which can be used directly for intake or/and intermediate cooling. They especially concern methanol-water or ethanol-water mixtures 108, or a methanol- or ethanol-containing cooling fluid. It is also possible to use methanol-ethanol-water mixtures 108 in all embodiments.

The term of mixture 108 will be used here because the product which is provided at the output 23 of a reactor 10 (FIG. 3) does not consist of 100% alcohol. It rather concerns a so-called physical mixture of methanol and water, ethanol and water, or methanol, ethanol and water. The following examples relate to methanol-water mixtures 108, but can also be applied to the other mentioned mixtures 108. The methanol and the ethanol preferably originate from different reactors or installations and can then be combined into a methanol-ethanol-water mixture 108.

The term of heat engine with internal combustion 62 (FIG. 4) shall be used here for internal combustion engines, i.e. gasoline engines, diesel engines and also (open) gas turbines.

Figure 1:
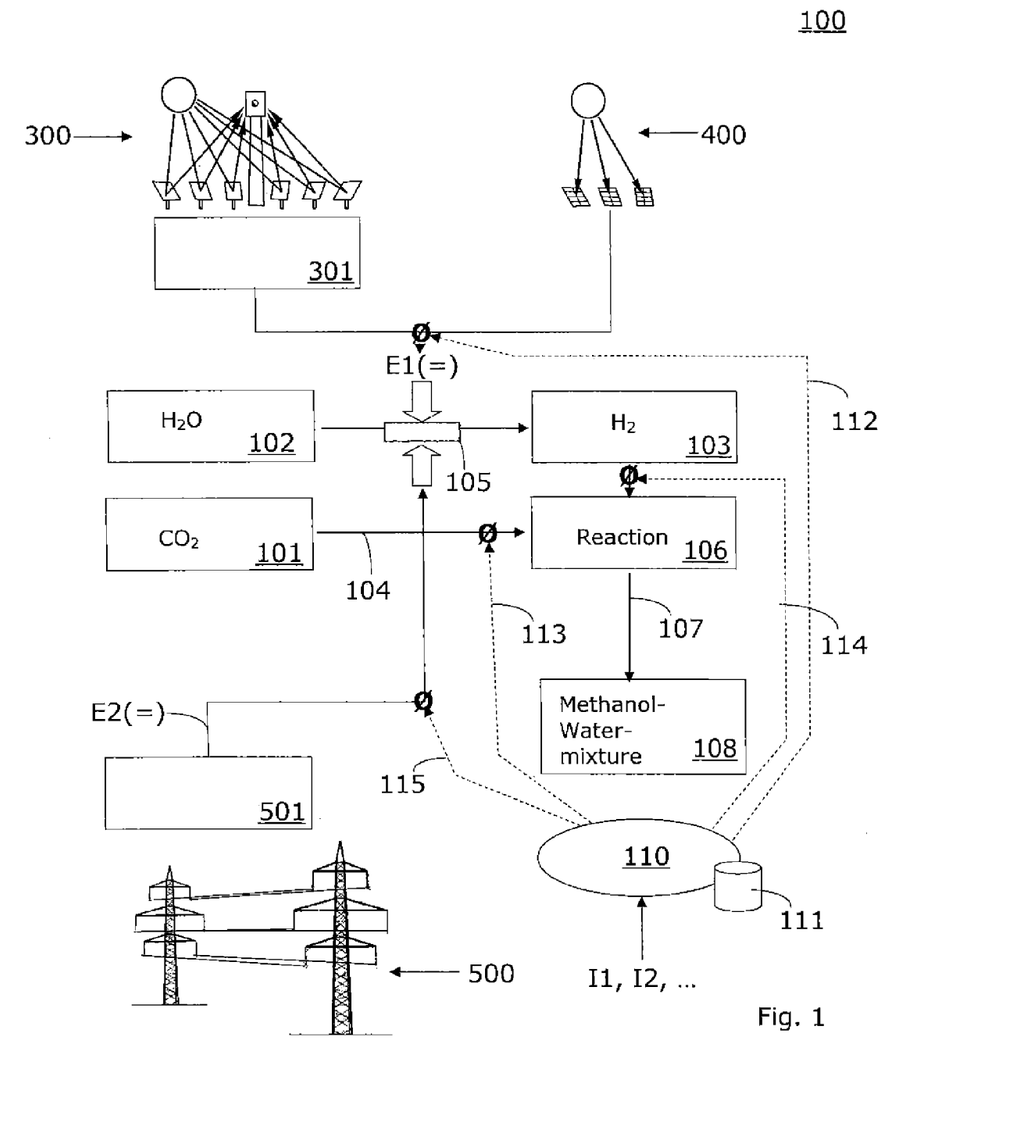
FIG. 1 shows a diagram representing the principal steps of the method according to one of the aforementioned international patent applications, and a Silicon-Fire installation respectively.

FIG. 1 shows a schematic block diagram with the most important parts/components, and method steps respectively, of a commercial Silicon-Fire installation 100 according to one of the previously mentioned international patent applications. This installation 100 is configured in such a way that a method for providing storable and transportable alcohol-containing cooling fluid mixture 108 can be carried out. The respective method is based on the following principal steps.

Carbon dioxide 101 is provided as a carbon supplier. The electrical DC energy E1 which is required for producing hydrogen 103 is produced as far as possible by means of renewable energy technology and provided to the silicon-fire installation 100. Solar thermal installations 300 and photovoltaic installations 400 which are based on solar modules are especially suitable as renewable energy technology. It is also possible to use hydroelectric or wind power or geothermal energy.

According to FIG. 1, water electrolysis 105 by using electrical DC energy E1 is used in order to produce hydrogen 103 as an intermediate product.

An economically and ecologically optimal combination of regenerative power supply (e.g. by the installations 300 and/or 400) and conventional power supply (illustrated here by a part of an integrated network 500) will be realized in the Silicon-Fire installation 100. Said Silicon-Fire installation 100 therefore provides to utilize the regenerative electrical energy E1 substantially directly as produced for chemical reactions (in this case the electrolysis reaction 105) and to therefore chemically bind and store the same. A further fraction of the required energy will be drawn for example from the integrated network 500. This fraction will be converted into DC (energy) E2. For this purpose, a respective converter 501 will be used, as schematically indicated in FIG. 1. The respective installation parts or components will also be designated here as energy supply installation 501.

The energy supply of the installation 100 according to FIG. 1 will be controlled and regulated by means of an intelligent installation control unit 110. In principle, the respectively available excess energy fraction E2 will be taken from the integrated network 500, whereas the other energy fraction (here E1) will be taken as far as possible from an (installation-related) solar power plant 300 and/or 400 (and/or from a wind power plant and/or from a hydro electric power plant and/or from a geothermal power plant). This principle allows the operator of the Silicon-Fire installation 100 to include additional technical and economic parameters in the control of the installation 100. These parameters concern the so-called input quantities I1, I2, etc, which are included in the decisions made by the control unit 110. A part of the parameters can be predetermined within the control unit 110 in a parameter storage unit 111. Another part of the parameters can come from the outside. In this case, pricing and availability information from the operator of the integrated network 500 can be included for example. As a result of the control unit 110, the method in accordance with the invention can be carried out in the installation 100 in such a way that the cooling fluid mixture 108 which is provided on the output side fulfils the desired requirements with respect to the mixture ratio and/or $CO_2$ neutrality.

Figure 2:
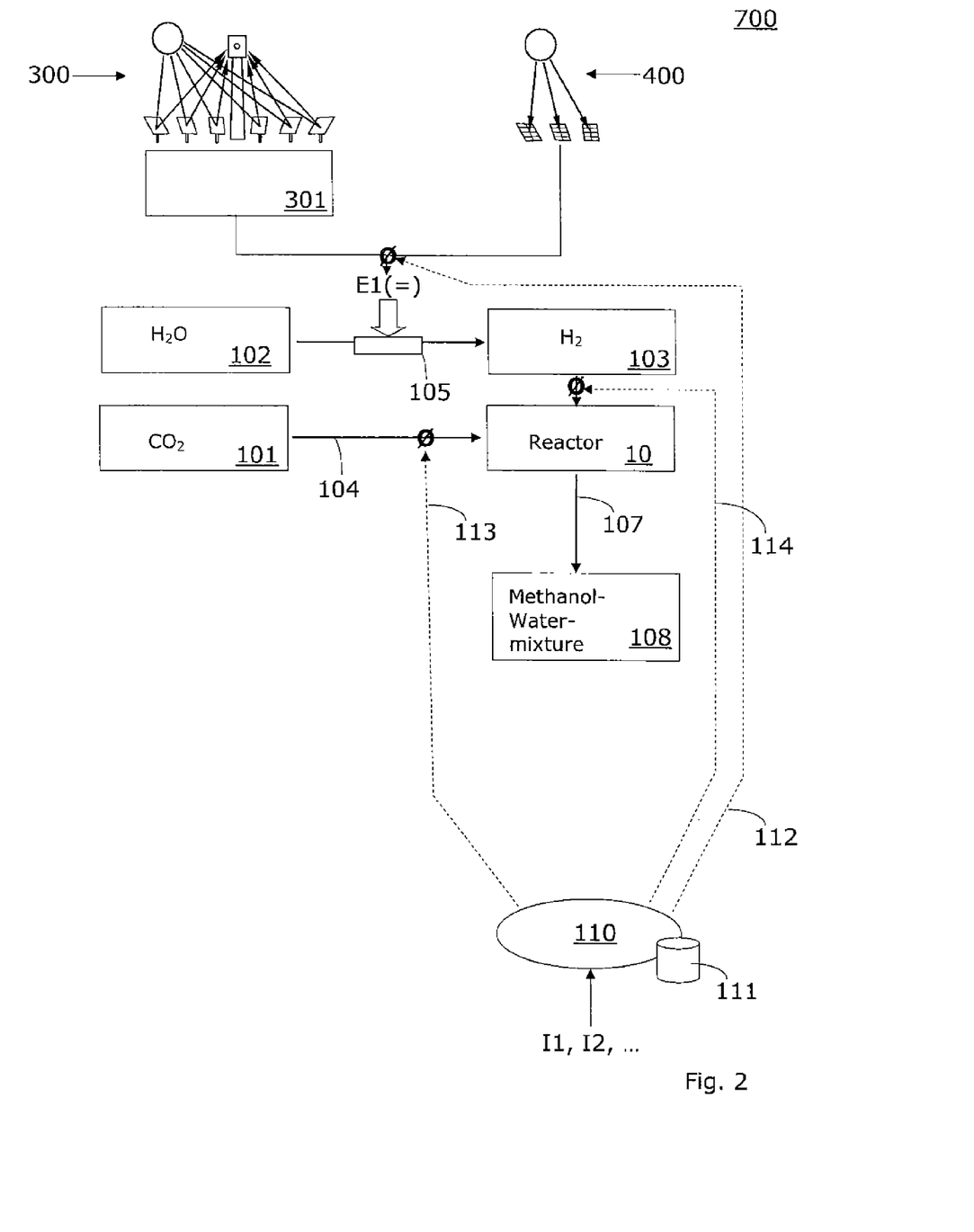
FIG. 2 shows a diagram representing the principal steps of the method in accordance with the invention, and a Silicon-Fire installation respectively.

FIG. 2 schematically shows a further installation 700, which can be used to perform the method in accordance with the invention. A part of this installation 700 corresponds to the installation 100 according to FIG. 1. Reference is therefore made to the preceding description of the respective elements.

As described above, high-purity hydrogen 103 is also produced in this installation 700 by water electrolysis 105, said hydrogen being converted here into a methanol-water mixture 108 for example. The energy for this purpose is obtained in this embodiment entirely or substantially (preferably up to more than 80%) from regenerative energy sources 300 and/or 400 (or from other regenerative energy sources).

A number of control or signal lines can be provided, as shown by way of example with respect to the lines 112, 113, 114 and 115. These lines 112, 113, 114 and 115 control the energy or mass flows of the installation 100 or 700.

So-called software-based decision-making processes are implemented in the installation control unit 110. A processor of the control unit 110 executes control software and makes programmed decisions on the basis of parameters. These decisions will be converted into switching or control commands, which produce the open-loop/closed-loop control of energy and mass flows via the control or signal lines 112, 113, 114, 115 for example. The control unit 110 allows conducting the method in the installation 100 in such a way that the cooling fluid mixture 108, which is provided on the output side, fulfils the desired requirements concerning the mixture ratio and/or $CO_2$ neutrality.

Figure 4:
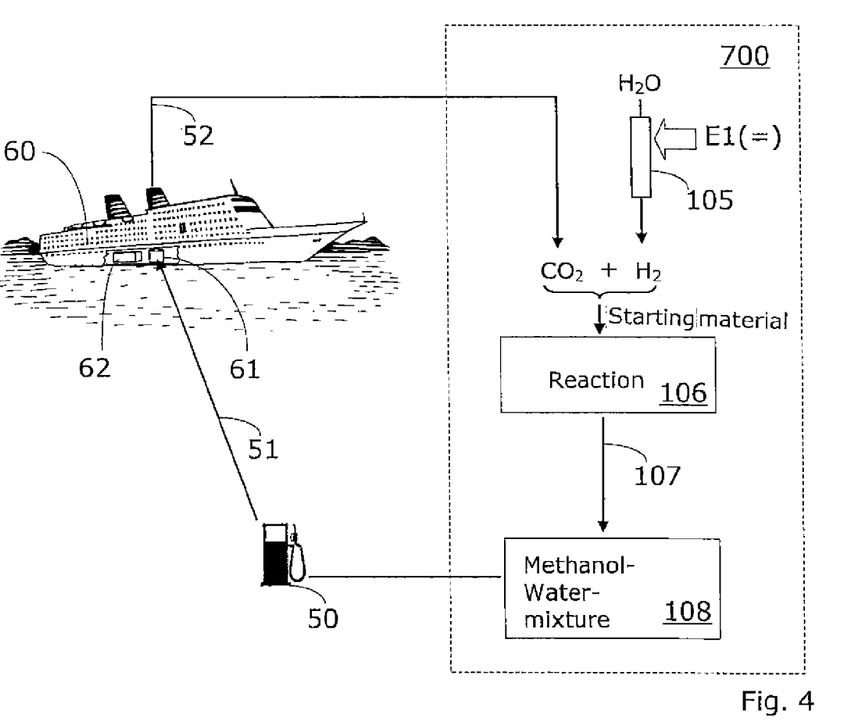
FIG. 4 shows a highly schematic view of the overall method in accordance with the invention.

In accordance with the invention, carbon dioxide 101 is used as a gaseous carbon supplier, as schematically indicated in FIG. 1, FIG. 2 and FIG. 4. Preferably, the carbon dioxide 101 is taken from a combustion process or an oxidation process via $CO_2$ separation (e.g. a Silicon-Fire fluid-gas cleaning system). The carbon dioxide 101 can also be separated from the raw natural gas and be made available. The carbon dioxide 101 can also come from other sources. Preferably, the carbon dioxide 101 will also be provided by a pipeline, a steel cylinder or a tank. FIG. 4 schematically shows that the $CO_2$ can originate from the exhaust gases of a vehicle, e.g. a ship 60, which is at anchor in the harbor and whose systems are running.

Figure 3:
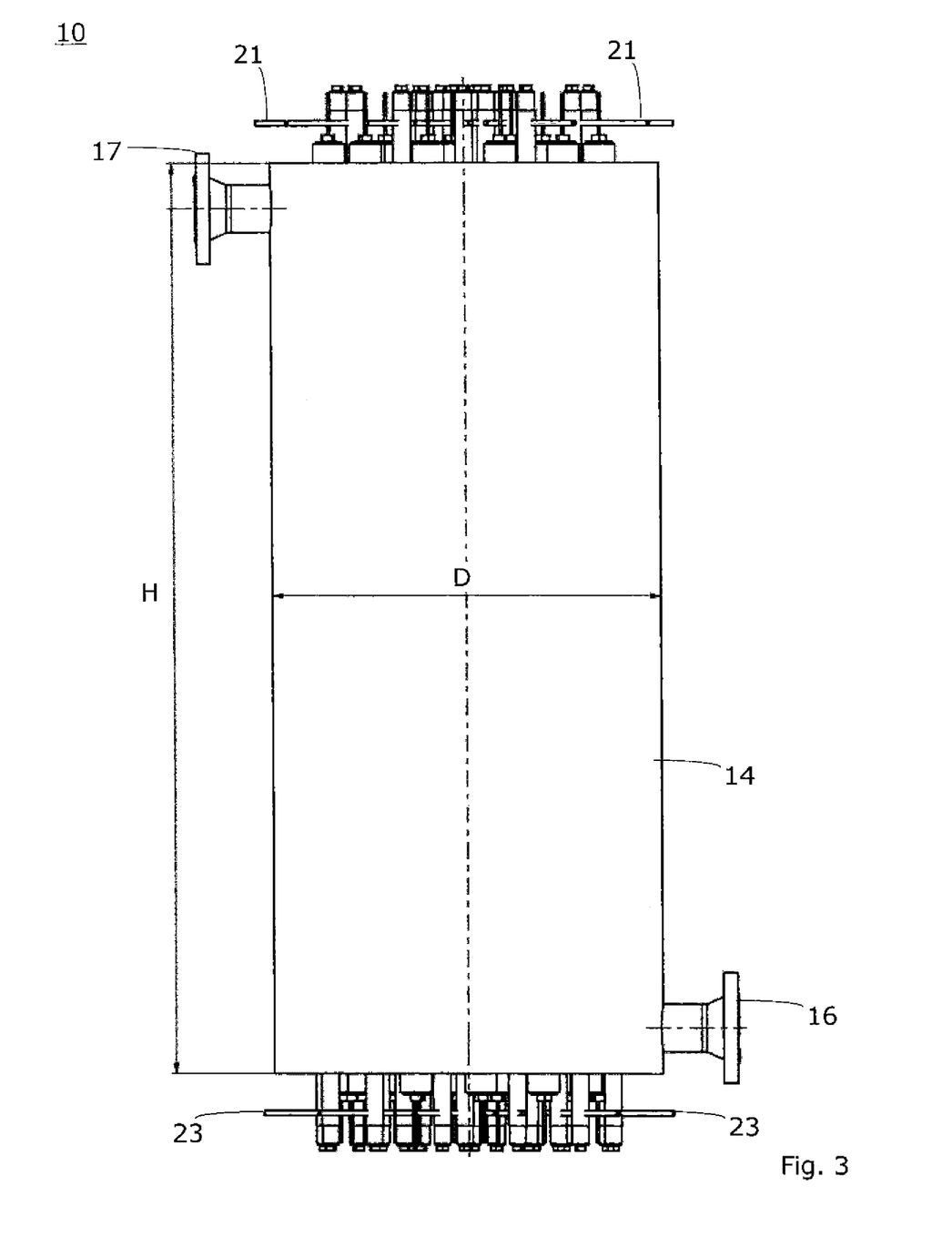
FIG. 3 shows a lateral outside view of a reactor which can be used in a method in accordance with the invention.

Furthermore, electrical DC energy E1 is further provided in the installation 700 shown in FIG. 2 (the same also applies to the installation in FIG. 4). The DC energy E1 will preferably be generated in a regenerative manner to a substantial extent (e.g. by one of the installations 300 and 1400 in FIG. 2). The DC energy E1 will be used in the illustrated installation 700 for performing water electrolysis in order to generate hydrogen 103 as an intermediate product. The electrolysis installation or the performance of such electrolysis is indicated in FIG. 1, FIG. 2 and FIG. 4 by reference numeral 105. The carbon dioxide 101 is guided together with the hydrogen 103. The respective gas is designated here as starting material AS (FIG. 4). The starting material AS is made to react (methanol synthesis in a reactor 10, as shown in FIG. 3 for example) in order to convert the gaseous (intermediate) products 101, 103 into a methanol-water mixture 108 for example. The reaction will be carried out in the reactor 10. The removal or provision of the methanol-water mixture 108 is shown in FIG. 1, FIG. 2 and FIG. 4 by the reference numeral 107.

Further principal details of the method in accordance with the invention and the respective silicon-fire installation 700 will be described below.

In order to produce hydrogen 103 as an intermediate product, water electrolysis by using direct current E1 is suitable. The required hydrogen 103 will be produced in an electrolysis installation 105 by the electrolysis of water $H_2O$ according to the following equation:

$$H_2O - 286.02\ kJ = H_2 + 0.5\ O_2 \quad \text{(Reaction 1)}$$

The required (electrical) energy E1 for this reaction of 286.02 kJ/mol corresponds to 143010 kJ per kg of $H_2$.

The synthesis of the methanol-water mixture 108 ($CH_3OH$) can occur as follows in the reactor 10 of the Silicon-Fire installation 700 according to the exothermal reaction between carbon dioxide 101 ($CO_2$) and hydrogen 103 ($H_2$):

$$CO_2 + 3\ H_2 = CH_3OH + H_2O - 49.6\ kJ \text{ (methanol-water mixture, vaporous)} \quad \text{(Reaction 2)}$$

The obtained heat of reaction of 49.6 kJ/mol=1550 kJ per kg of methanol=0.43 kWh per kg of methanol 108 will be discharged from the respective reactor 10. For this purpose, the reactor 10 comprises a fluid chamber 14 (see FIG. 3 or 7A for example), i.e. the reactor 10 is surrounded by a reactor shell and is cooled by the fluid (preferably water).

Typical synthesis conditions in the synthesis reactor 10 are approximately 50 to 80 bars and approximately 270° C. The reaction heat can be "transferred" to other elements of the installation for example.

The methanol-water synthesis is performed in accordance with the invention by using a catalyst in order to keep the reaction temperature, reaction pressure and reaction duration at a low level in comparison with other methods and in order to ensure that a fluid methanol-water mixture 108 is obtained as a reaction product which is suitable as a cooling fluid.

If the Silicon-Fire installation 700 is situated close to a $CO_2$ source (e.g. a ship 60, as shown in FIG. 4), liquefying of $CO_2$ for transport can be avoided. Otherwise, it is relatively simple to liquefy the $CO_2$ according to the state of the art and to transport said gas even over long distances to a Silicon-Fire installation 700. In the case of omitting the liquefying and optionally the storage and transport over longer distances, the $CO_2$ is available in many cases in a neutral manner in terms of effect on costs under consideration of $CO_2$ avoidance credits. Even in the case of transport, the costs for "acquiring" the $CO_2$ are relatively low.

It is shown in FIG. 2 on the basis of the dashed arrow 112 originating from the control unit 110 that the control unit 110 controls the energy flow E1. The arrow 112 represents a control or signal line. Other possible control or signal lines 113, 114 are shown. The control or signal line 113 controls the quantity of $CO_2$ for example which is available for the reaction 106. If less hydrogen 103 is produced for example, then it is also necessary to supply proportionally less $CO_2$. The optional control or signal line 114 can control the quantity of $H_2$ for example. Such a control will make sense when there is a hydrogen buffer storage unit from which hydrogen 103 can be taken, even when at a given time no hydrogen or less hydrogen is produced by electrolysis 105 (or by using elementary silicon or metal).

Examinations have shown that it is especially economical and useful with respect to environmental protection when the Silicon-Fire installation 100 or 700 is configured or controlled in such a way that between 15% and 40% of the methanol-water mixture 108 are produced from regenerative energy, whereas further methanol-water mixture for supplementing to 100% is provided from other hydrocarbons (e.g. from methane gas).

An embodiment of the operating concept of the installation 100 or 700 is especially preferred which provides drawing cheap electrical power in off-peak periods from the integrated network 500 (as shown in FIG. 1).

As already described above, the methanol-water mixture 108 will be synthesized by using a starting material AS which contains the $CO_2$ gas 101 and hydrogen gas 103. The respective reactor 10 comprises a reactor element or preferably several reactor elements 15.m which are arranged in parallel with respect to each other, as described below in further detail. There is at least one gas inlet 21 on the reactor 10 for the starting material AS and a product outlet 23, as shown by way of example in FIGS. 3, 7A, 7B, 7C and 8.

The details of an especially preferred embodiment of a reactor 10 for the synthesis of the methanol-water mixture 108 are shown in FIG. 3. The statements made in the international patent application PCT/EP2010/064948 with application date 6 Oct. 2010 on the synthesis of methanol 108 can also be applied to the synthesis of other fluid hydrocarbons.

Figure 7A:
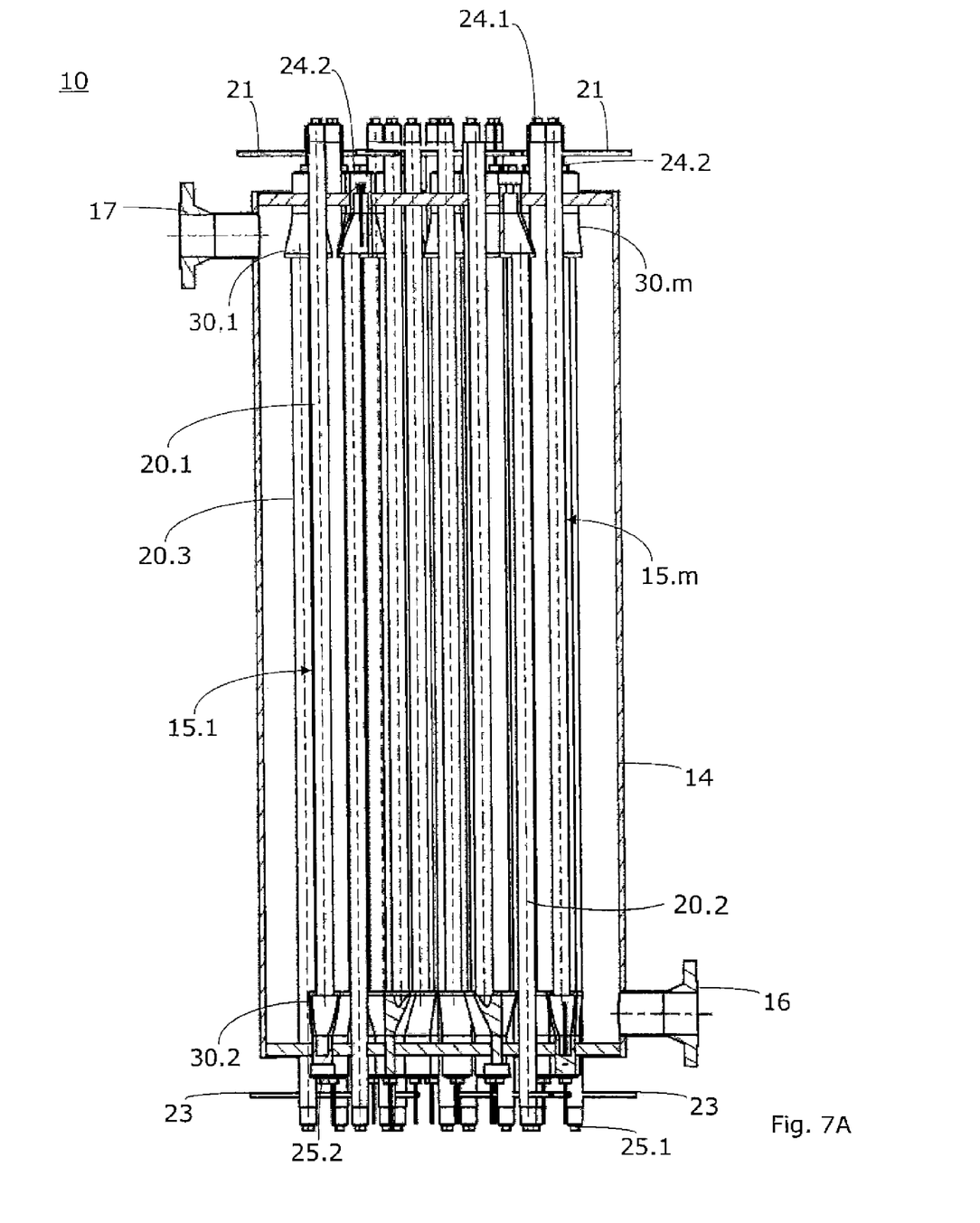
FIG. 7A shows a lateral sectional view (along the line of intersection A-A in FIG. 7B) of a reactor in accordance with the invention.
Figure 7B:
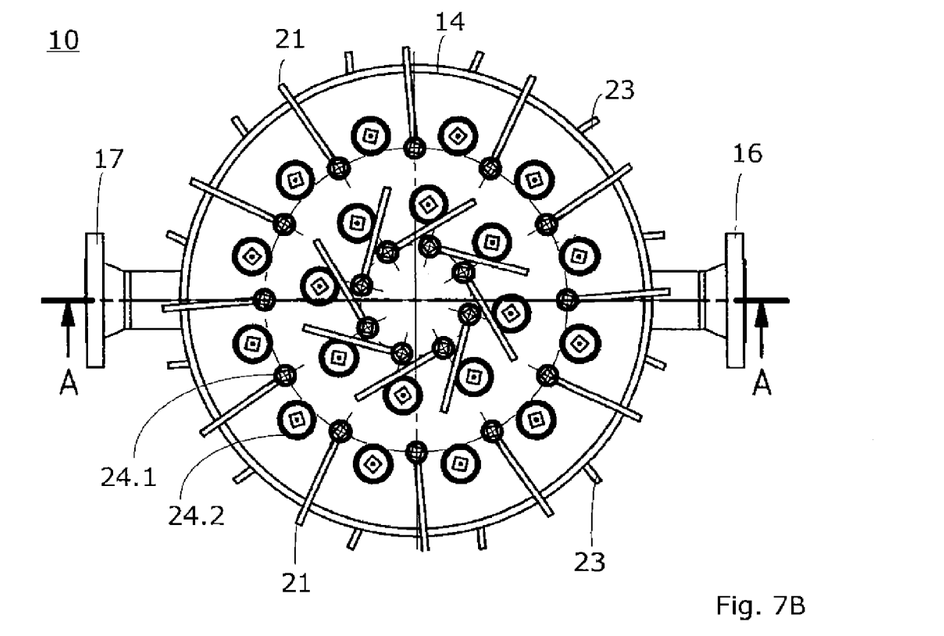
FIG. 7B shows a top view of the reactor according to FIG. 7A.
Figure 7C:
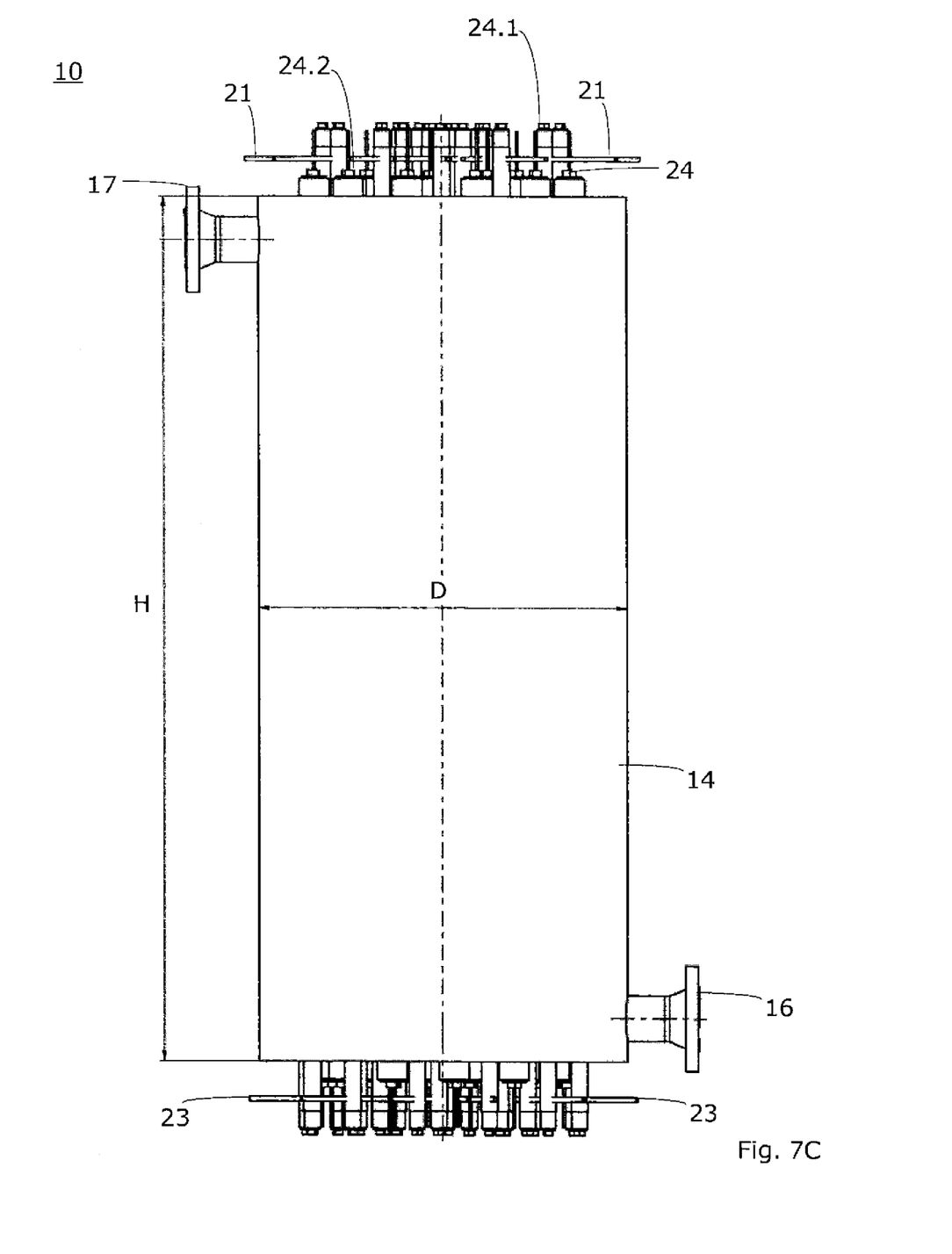
FIG. 7C shows a lateral external view of the reactor according to FIG. 7A.
Figure 8:
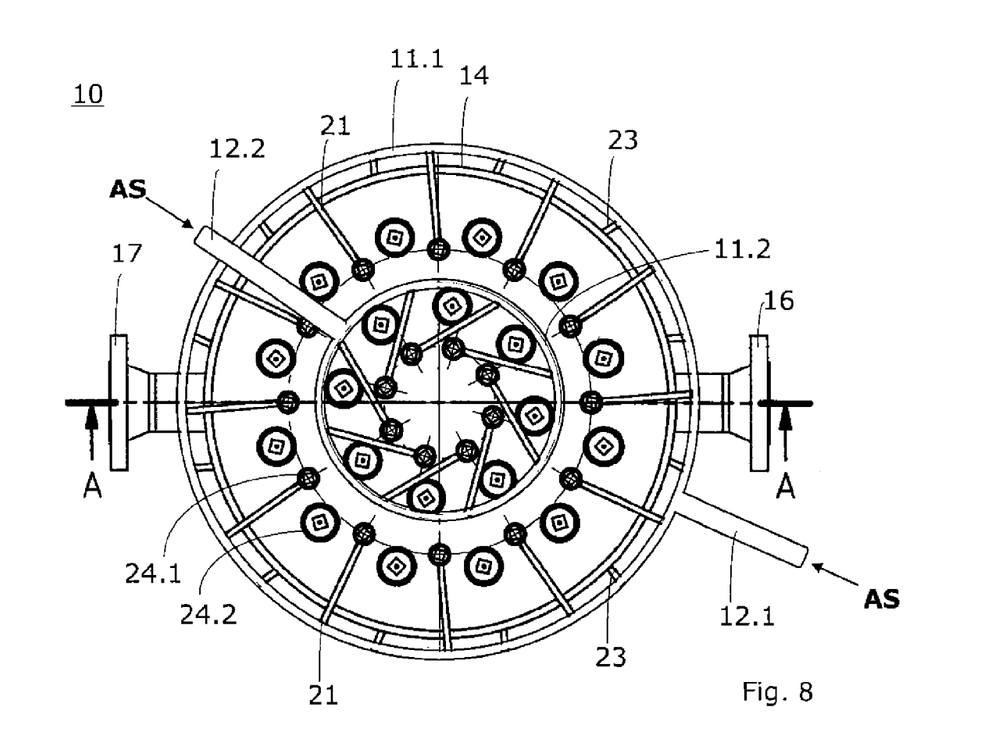
FIG. 8 shows a top view of a reactor according to FIG. 7A, wherein the two upper ring lines plus feed lines are indicated in schematic form.

The details of an especially preferred embodiment according to the international patent application PCT/EP2010/064948 are shown in FIGS. 7A to 7C. The reactor 10 was developed and optimized especially according to the problem to be solved. The reactor 10 comprises a bundle of reactor elements 15.1-15.$m$ (e.g. m=20) in this case. In this specific example, the reactor 10 comprises an inwardly disposed bundle with eight reactor elements 15.$m$ and an external bundle with twelve reactor elements 15.$m$ (i.e. m=20). In order to avoid disturbing the illustration in FIG. 7A to FIG. 7C by an excessive number of reference lines and reference signs, only a part of the elements was provided with reference lines and reference signs. Two reactor elements 15.1 and 15.$m$ of the external bundle are designated in FIG. 7A with reference numerals. The inwardly situated bundle is not visible because it is covered by the reactor elements 15.$m$ of the external bundle. Each reactor element 15.$m$ preferably comprises in all embodiments at least n=2 reactor tubes 20.1-20.$n$ (n is an integral number which is greater than or equal to 2). In the embodiment as shown in FIGS. 7A to 7C and 8, each reactor element 15.$m$ comprises n=3 reactor tubes 20.1, 20.2 and 20.3 (see FIG. 7A). In such an arrangement, which in the case of n=3 reactor tubes 20.1, 20.2 and 20.3 always comprises two deflection elements 30.1 and 30.2 (in this case two 180° deflection elements) per reactor element 15.$m$, a constellation is obtained in which the gas inlet 21 for the starting material AS sits at the upper end of the reactor 10 (as shown in FIGS. 7A, 7C and 8), and the product outlet 23 sits at the bottom end of the reactor 10 (as shown in FIGS. 7A, 7B and 7C).

The reactor 10 preferably comprises a fluid chamber 14 which is provided with a cylindrical shape here. The fluid chamber 14 surrounds the entire bundle of the reactor elements 15.$m$, wherein merely the upper and bottom ends of the reactor elements 15.$m$ protrude from the fluid chamber 14 (as shown in FIGS. 7A, 7B, 7C and 8). First and second filling openings 24.1, 24.2 and the gas inlets 21 on the input side and the product outlets 23 on the output side are situated outside of the fluid chamber 14. The fluid chamber 14 is used for providing an isothermal environment in a preferred operating mode of the reactor 10. For this purpose, a fluid (e.g. water or gas) can reach the fluid chamber 14 through a fluid feed 16. A fluid discharge 17 is provided on the fluid chamber 14 in order to discharge the fluid. It can be cooled or heated depending on the situation. Discharge openings 25.1, 25.2 (see FIG. 7A for example) are preferably also situated outside of the fluid chamber 14.

The advantage of an uneven number n (n=3 in this case) is that the input side and the output side are situated at opposite ends of the reactor elements 15.$m$ This provides space for the arrangement of a common input collector or distributor 11.1, 11.2 (e.g. in the form of a ring line, as shown in FIG. 8) on the one side and for the arrangement of the product outlet(s) 23 on the other side.

Preferably, the reactor 10 comprises in all embodiments two upper input collectors or distributors 11.1, 11.2 in form of an inner ring line 11.2 and an outer ring line 11.1, as shown in FIG. 8. The outer upper ring line 11.1 has a radius which is chosen in such a way that the gas inlets 21 of the outer bundle can be supplied evenly with the starting material AS by the outer upper ring line 11.1. A first feed line 12.1 can preferably be provided on the first upper ring line 11.1. The inner upper ring line 11.2 has a radius which is chosen in such a way that the gas inlets 21 of the inner bundle can all be supplied evenly with the starting material AS by the inner upper ring line 11.2. A second feed line 12.2 can preferably be provided on the inner upper ring line 11.2. It is also possible to supply all feed lines 21 of the inner reactor elements 15.$m$ and the outer reactor elements 15.$m$ by a common ring line which is used as a collector or distributor.

It is also possible to supply all inner reactor elements 15.$m$ and outer reactor elements 15.$m$ in all embodiments from above through a common pre-chamber (not shown in the drawings) which is used as a buffer for the even distribution of the gas AS.

FIG. 7B shows the top view of the reactor 10. The illustration shows that the gas inlets 21 of the outer bundle face radially to the outside. They all end in a common first radius. The gas inlets 21 of the inner bundle face to the outside in an oblique fashion, and all of them end in a common second radius which is smaller than the first radius. This kind of alignment and arrangement of the gas inlets 21 allows providing two ring lines 11.1 and 11.2, as schematically indicated in FIG. 8. The first upper ring line 11.1 has a radius which corresponds to the first radius in such a way that the gas inlets 21 of the outer bundle can all be supplied evenly with the starting material AS by the first upper ring line 11.1. A first feed line 12.1 can be provided on the first upper ring line 11.1. A second upper ring line 11.2 has a radius which corresponds to the second radius in such a way that the gas inlets 21 of the inner bundle can all be supplied evenly with starting material AS by the second upper ring line 11.2. A second feed line 12.2 can preferably be provided on the second upper ring line 11.2.

FIGS. 7B and 8 show that the filling openings 24.1, 24.2 are preferably freely accessible from above in order to enable simple filling with the catalyst and/or venting and/or purging (e.g. with inert gas).

FIG. 7C shows the reactor 10 from the outside. The reference numerals are the same as in the other drawings. The fluid chamber 14 has an envelope diameter D in this case (as also in FIG. 3), which can be approx 1 m for example. The height H of the fluid chamber 14 is approximately 2.2 m in this case for example. As a result, the reactor elements 15.$m$ can be housed in the fluid chamber 14 which respectively have a total reaction section of approximately 5.7 m for example. The total reaction section of approximately 5.7 m is composed in the illustrated preferred embodiment of the respective partial sections because each of the reactor elements 15.$m$ comprises n=3 reactor tubes 20.1, 20.2 and 20.3.

When passing or pressed through the reactor tube(s) 20.1 to 20.3 of the reactor 10, the starting material AS will successively be converted into a methanol-containing mixture 108 (known as alcohol-containing cooling fluid). The methanol concentration of the reaction fluid is at zero on the input side of the reactor 10 and the concentration of the gaseous starting material AS is at approximately 100%. In the direction of the output side of the reactor 10, the respective concentrations will shift in the opposite direction until a methanol-containing mixture 108 is formed at the output (at the product outlet 23) with a predetermined methanol concentration (preferably a methanol-water mixture at a ratio of 1:2).

The reactor 10 preferably supplies approximately 64% by mass (69.2% by volume) of methanol as raw methanol and 36% by mass (30.8% by volume) water.

The cooling fluid mixture 108 should especially preferably contain between 5 and 50% by mass of methanol and the remainder of water. A cooling fluid mixture 108 is especially suitable with approximately 10 to 15% by mass of methanol in order to keep the costs of the cooling fluid mixture 108 and the loading of the heat engine 62 at a low level.

The reactor 10 or the reactor elements 15.$m$ of the reactor 10 comprise a catalyst for the synthesis of the methanol-water mixture 108 in all embodiments.

Preferably, a control of the reactor 10 will be used in all embodiments which initially during the "start-up" of the reactor 10 supplies warm fluid to the fluid chamber 14 in order to start the synthesis reaction. Subsequently, a cooled fluid is preferably supplied in order to discharge reaction heat which is obtained in excess thermal synthesis and to create an isothermal environment in this way.

Preferably, the fluid chamber 14 is configured in all embodiments in such a way that at least the reaction sections of the reactor 10 which are filled with the catalyst lie in the isothermal environment.

FIG. 3 shows the reactor 10 from the outside.

The starting material AS is preferably preheated in all embodiments of the invention and/or supplied with increased pressure through the feed lines into the reactor 10. The pressure and the temperature depend on the type of the catalyst. Preferably, the temperature lies in the range of between 100 and 350° C. The pressure typically lies between 10 and 150 bars. That is why it can be stated that the starting material AS is pressed through the reactor 10 in preferably all embodiments under predetermination of a pressure of between 10 and 150 bars on the input side.

The reactor 10 is especially suitable for the synthesis of a regenerative methanol-water mixture 108 of carbon dioxide $CO_2$ and hydrogen $H_2$, which is generated via (endothermic) electrolysis of water with regenerative electrical energy E1 according to reaction 1, as already mentioned above.

$$H_2O-286.02 \text{ kJ/mol}=H_2+0.5O_2 \quad \text{(Reaction 1)}$$

The exothermal methanol-water synthesis (reaction 2, as already mentioned above) is explained by the summation formula:

$$CO_2+3\ H_2=CH_3OH+H_2O-49.6\text{ kJ (gaseous methanol).} \quad \text{(Reaction 2)}$$

In practice, the available regenerative electrical energy E1 will preferably be utilized to the maximum extent for generating the "regenerative" methanol-water mixture 108 according to the reactions 1 and 2, and the optional fraction of methanol produced in a "fossil" manner will be set up to the possible maximum value depending on economic and ecological targets and boundary conditions, e.g. according to a desired specific $CO_2$ emission of the "total" methanol-water mixture at combustion or according to the current price and availability of natural gas or according to the "total" methanol quantity to be produced or according to the prices of regenerative and fossil methanol fractions.

It needs to be noted that it is obvious that in all embodiments other methods of synthesis and other reactors 10 or installations can be used, and that the synthesis can be carried out with regenerative energy and/or with the regenerative starting material AS. The use of regenerative energy and regenerative starting materials AS is preferred.

It is especially advantageous that the "regenerative" methanol-water mixture 108 and the "fossil" methanol-water mixture (if present) can be obtained separately in different reactors and can either be supplied separate from one another or can be mixed after occurrence and optional intermediate storage in any desired fractions, so that the Silicon-Fire installation 100 can supply purely "regenerative" methanol-water mixture 108 and purely "fossil" methanol-water mixture, but also random mixtures of the same, in order to enable the marketing thereof as regenerative cooling fluid for the intake or intermediate cooling with permissible fossil fraction or permissible specific $CO_2$ emissions.

The use of the invention in connection with a method for methanol-water synthesis is especially advantageous which operates at low pressures of between 10 and 150 bars (preferably at approximately 80 bars).

The principle of the invention can also be applied to large-size installations, but it is especially suitable for small local installations which are installed in a sea freight container.

In accordance with the invention, $CO_2$ 101 is used as the starting material and the carbon supplier for the methanol-water synthesis in reactor 10. The following are preferably used as $CO_2$ sources: steam-reforming installations, $CO_2$ separation installations for raw natural gas, lime-kilns, calcination plants for soda, fermentation plants for bioethanol, seawater desalination plants, large-size firing plants for fossil fuels (e.g. firing plants for power plants), internal combustion engines of vehicles/ships 60 and other heat machines 62 or combustion processes which emit relatively large quantities of $CO_2$.

Depending on the synthesis reactions, copper-based catalysts (e.g. CuO catalysts) or zinc oxide catalysts (e.g. ZnO catalysts) or chromium oxide-zinc oxide catalysts can be used for example. All other known catalysts are also suitable for use in a reactor 10. Fixed-bed catalysts or fluid-bed catalysts are especially suitable. The catalyst can also comprise a suitable carrier (e.g. carbon, silicate, aluminum (e.g. $Al_2O_3$) or ceramic). Instead of the mentioned "metallic" catalysts it is also possible to use an organic catalyst.

In preferably all embodiments, the catalyst has a grain, ball or particle size of between 1 and 10 mm A grain, ball or particle size of between 3 and 8 mm is especially preferable.

Carbon dioxide as a carbon supplier can also be taken in accordance with the invention from raw natural gas, which depending on the natural gas source can have a carbon dioxide fraction of more than 10%. After extracting the raw natural gas, gas separation (by means of gas washing technology or another gas separation technology) is currently typically performed in order to separate the $CO_2$ from the actual natural gas. This $CO_2$ is mostly emitted to the atmosphere. In accordance with the invention, the $CO_2$ which is present in substantially pure form can be used as a carbon supplier 101.

Figure 5:
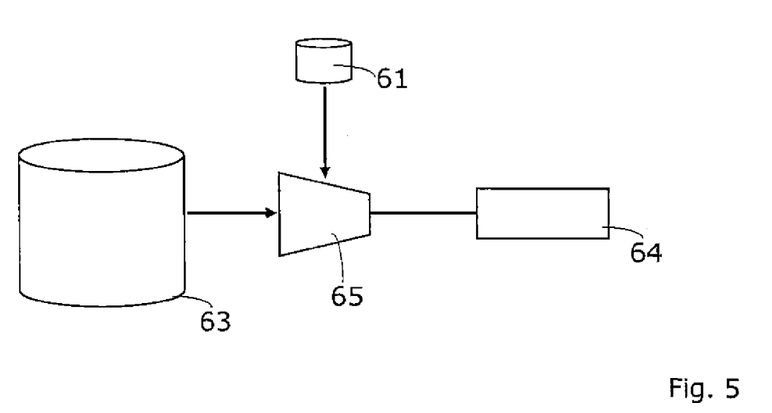
FIG. 5 shows a schematic view of an apparatus which comprises a compressor with intermediate cooling.

In accordance with the invention, the regenerative or the regenerative and fossil methanol-water mixture 108 is used as a cooling fluid for intake or intermediate cooling, as indicated in FIG. 5.

The methanol-water mixture 108 is especially suitable for use as an active cooling fluid in an auxiliary unit 65 (compressor) of an internal combustion engine 62, e.g. in an intermediate cooling unit 65 of a vehicle/ship 60. The term of "active cooling fluid" shall indicate that the alcohol fraction will be co-combusted in the internal combustion engine 62.

The compressor 65 shall be regarded as a component of the internal combustion engine 62.

The method for providing and consuming a storable and transportable alcohol-containing cooling fluid 108 therefore comprises the following steps:

Providing (step 104 in FIG. 1, 2) a gas with a carbon dioxide fraction ($CO_2$) 101 as a carbon supplier. The provision can occur for example by direct or indirect withdrawal via a connection 52 (see FIG. 4).

Providing a hydrogen fraction 103 ($H_2$). The hydrogen fraction 103 will preferably be produced by electrolysis 105 from water ($H_2O$), as described above.

Providing a starting material AS which comprises the carbon dioxide fraction 101 and the hydrogen fraction 103.

Introduction of the starting material AS into a reactor 10 (as shown in FIG. 3 for example).

Passage or pressing of the starting material AS through a reaction section of the reactor 10 which is equipped at least partly with a catalyst. The alcohol-containing cooling fluid will be synthesized in this step in a catalytic synthesis process. Providing the alcohol-containing cooling fluid 108 at an output end 23 of the reactor 10, wherein the alcohol-containing cooling fluid 108 concerns a mixture of an alcohol fraction (e.g. methanol and/or ethanol) and a water fraction.

Using this alcohol-containing cooling fluid 108 in an internal combustion engine 62 (e.g. in an internal combustion engine) which is supplied with air or a fuel-air mixture, wherein the alcohol-containing cooling fluid 108 will be used for cooling the air or the fuel-air mixture by evaporation of the alcohol-containing cooling fluid 108.

The fuel can concern a diesel fuel, a fuel similar to diesel (e.g. biodiesel), a gasoline fuel, a hydrocarbon gas or a special fuel (e.g. kerosene).

The intercooling of the gas or the charge air of the internal combustion engine 62 with respective increases in power and efficiency and without pressure loss can occur by the introduction/injection of the cooling fluid 108 into the air or the fuel-air mixture, wherein the cooling fluid 108 will evaporate and will cool the air or the fuel-air mixture according to its evaporation heat.

Since the cooling fluid 108 is combustible, it participates in the subsequent combustion process in the thermal conversion installation 64 under respective delivery of mechanical power and/or heat. The cooling fluid will therefore also be mentioned herein as active cooling fluid.

In the case of diesel engines, it is also possible to supply a respective part of the primary fuel in form of a fluid energy carrier (such as ethanol or methanol) which is otherwise not suitable for diesel engines due to insufficient ignition properties (e.g. too low cetane number). Methanol-water mixtures 108 are especially suitable for the aforementioned form of intake or intermediate cooling due to their relatively high evaporation heat.

The relations in the injection of methanol for intercooling the charge air will be illustrated on the basis of an example of a truck diesel engine.

Assumed parameters: engine data of the four-stroke turbo diesel engine at nominal power:

| | |
|---|---|
| Power: | 220 kW |
| Boost pressure (absolute): | 2.4 bars |
| Outside air temperature: | 21.0° C. |
| Air temperature before compressor: | 31.0° C. |
| Air temperature after compressor and before intercooling: | 117.0° C. |
| Air temperature after intercooling: | 40.0° C. |
| Engine efficiency: | 43% |
| Diesel fuel consumption of engine (Diesel fuel mass flow): | 0.0119 kg/s |
| Stoichiometric air-fuel ratio: | 2 |
| Air-fuel mass ratio: | 14.9 |
| Air consumption of engine (air-mass flow): | 0.177 kg/s |
| Isobaric specific thermal capacity of air: | 1.0 kJ/(kg · K) |
| Thermal value of diesel fuel: | 43.0 MJ/kg |
| Thermal value of methanol: | 19.9 MJ/kg |
| Specific evaporation heat of methanol (at 65° C.): | 1099 kJ/kg |

The following energy balance applies to the cooling of the charged air from 117° C. to 40° C. (by 77 K):

Mass flow of air×temperature difference of air×isobaric specific thermal capacity of air=mass flow of methanol×specific evaporation heat of methanol.

It follows from this: mass flow of methanol=0.0124 kg/s according to a thermal value flow of 0.0124 kg/s×19.9 MJ/kg=0.247 MJ/s, which replaces the respective diesel fuel thermal value flow.

The original diesel fuel thermal value flow is 0.0119 kg/s× 43 MJ/kg=0.512 MJ/s, of which 0.247 MJ/s are replaced by methanol, leaving a diesel fuel thermal value flow of 0.265 MJ/s or a diesel fuel mass flow of 0.00616 kg/s.

As a result, according to the methanol injection as described above by way of example the diesel fuel supplies 52% of the entire thermal value mass flow and the methanol supplies 48%.

In the case of intercooling (intermediate cooling) of the charge air by 77 K with methanol, the internal combustion engine 62 would be supplied approximately half the fuel energy via diesel fuel as the primary fuel, which (as is usually the case in the diesel process) will combust according to the "injection law" in the combustion chamber during the working cycle at approximately constant pressure (with enlargement of the combustion chamber by the piston movement), whereas the other half of the fuel energy will be supplied via the methanol, which (premixed with the combustion air in the intermediate cooler 65) will be ignited at the moment of the first ignition of the injected diesel fuel and will combust in an explosive manner with respective rapid rise in pressure in the combustion chamber 62 of the internal combustion engine and with mechanical and thermal loading of the engine components.

A diesel engine that is not designed accordingly will not withstand this "mixed operation" between gasoline and diesel process over prolonged periods of time. That is why the fluid 108 contains from half to two-thirds water in addition to methanol according to the invention, i.e. a mixture 108 will be used which was produced in the described manner.

In the injection/addition of the methanol-water mixture 108 for charge air cooling, the regenerative energy fraction of 5.75% in the vehicle fuel in charged gasoline and diesel engines as required by EU and national regulations can be achieved and exceeded without the addition of bioethanol or biodiesel to the fuel.

The aforementioned regenerative energy fraction of 5.75% can also be achieved in charged standard gasoline and diesel engines with charge air coolers by additional injection of a methanol-water mixture 108 after the charge air cooler and by the resulting additional cooling of the charge air.

5.75% energy fraction in the fuel of the aforementioned diesel engine with a total fuel heating value flow of 0.512 MJ/correspond to 0.0256 MJ/s or a methanol mass flow of 0.0256 MJ/s : 19.9 MJ/kg=0.00129 kg/s=1.29 g/s=4.63 kg/h.

The additional cooling of the charge air after the charge air cooler is 8.0 K as a result of methanol injection, which leads to a noticeable increase in power and efficiency of the internal combustion engine 62.

The injection of a methanol-water mixture 108 for charge air cooling offers a possibility for easily retrofitting the widely used charged gasoline and diesel internal combustion engines for the purpose of widely exceeding the currently demanded 5.75% regenerative energy fraction in vehicle fuels without the admixture of bioethanol or biodiesel to the primary fuel, which additionally includes the resulting noteworthy increase in power and efficiency of the internal combustion engine 62.

Further preferred aspects of a method in accordance with the invention will be described below. Reference is hereby made to the schematic FIG. 4.

The mixture 108, which is provided at the output end 23 of the reactor 10, preferably comprises methanol as the alcohol fraction. In all embodiments, the mixture ratio of methanol to water is preferably between 5% by mass to 95% by mass and 50% by mass to 50% by mass. Especially good results are achieved in intermediate cooling in this manner.

The mixture ratio of methanol to water preferably comprises in all embodiments less than 30% by mass of methanol and more than 70% by mass of water.

A mixture ratio of methanol to water of between 10 and 15% by mass of methanol and 90 and 85% by mass of water is especially suitable.

If the water fraction of the mixture 108 which is used needs to be higher than the water fraction of the mixture 108 which is provided at the output end 23 of the reactor 10 in an integrated process, the water fraction of the mixture 108 can subsequently be increased by adding additional water.

Since the cooling fluid 108 comprises an alcohol fraction, said alcohol fraction takes part in the combustion in the internal combustion engine 62 when the cooling fluid 108 is introduced into the charge air or the fuel-air mixture of the internal combustion engine 62. This means that the alcohol fraction of the cooling fluid 108 takes part in the combustion in the internal combustion engine 62 together with the primary fuel.

The quantity of the cooling fluid 108 which is used will be controlled according to demand in all embodiments.

Preferably, the cooling fluid 108 is stored in all embodiments in an intermediate step in a (secondary) tank 61 of a vehicle 60 and taken when required from the tank 61 of the vehicle 60 and supplied to the internal combustion engine 62 for intake or intermediate cooling, as shown in FIG. 4.

Preferably, the method will be used in intake or intermediate cooling in a ship 60, a road or off-road vehicle (e.g. a bus, truck or special-purpose vehicle), or an aircraft.

The invention is especially used in a harbor, as schematically indicated in FIG. 4. A ship 60 which is docked in the harbor typically allows its generators and other units to run in order to supply the ship 60 with the required power. This procedure leads to very strong emissions. In accordance with the invention, the docked ship 60 can comprise a capturing apparatus for capturing $CO_2$. The withdrawal of the $CO_2$ is schematically shown in FIG. 4 by the connection 52. The hydrogen can be provided via electrolysis 105 from water, as shown in FIG. 4. The gas mixture (starting material AS) will be synthesized in a reactor (e.g. in a reactor 10 according to FIG. 3) in a catalytic manner into a methanol-water mixture 108. Said mixture 108 can be filled into a (secondary) tank 61 of the ship 60. Refueling is illustrated by a fuel pump 50 and a line 51. The internal combustion system 62 (e.g. a diesel engine of the ship 60) comprises means in order to introduce the cooling fluid 108 into the air flow or the fuel-air mixture. The emissions and the consumption of the ship 60 can be reduced by this measure.

The intermediate cooling can also be used during compression in a gas turbine installation, as described above. Such a gas turbine installation comprises in this case at least one compressor 65, a combustion chamber and a turbine. The combustion chamber forms a heat conversion installation 64 together with the turbine. The first compressor 65 can be provided with an air intake cooling or/and intermediate cooling which is supplied with the alcohol-water mixture 108, as described. The alcohol-water mixture 108 can be supplied from the secondary tank 61.

The advantages of the invention are among other things that the overall efficiency and the power of the internal combustion engine 62 can be increased by the intake and/or intermediate cooling. The ecological balance of the internal combustion engine 62 is improved by the increased efficiency because fewer emissions are produced in comparison with the obtained power.

It is an advantage of the invention that the respective intake and intermediate cooling can be retrofitted.

The system in accordance with the invention for intake and intermediate cooling preferably comprises in all embodiments a secondary tank 61, an apparatus for injecting or introducing the cooling fluid 108, and means for including the mentioned components into an open-loop or closed-loop control unit of the internal combustion system 62.

The system in accordance with the invention for intake and intermediate cooling is therefore a heat transfer system which in the intake passage or in the compressor 65 of an internal combustion engine 62 reduces the temperature of the medium supplied to the machine 62 (air or fuel-air mixture) by injecting or introducing the cooling fluid 108.

The cooling fluid 108 can be used in a turbo-engine, compressor motor or an aspirating engine for intake or intermediate cooling. The alcohol fraction of the cooling fluid 108 is used as an additional fuel and oxygen carrier, which is especially advantageous for diesel engines for which alcohols are not suitable as a primary fuel due to the insufficient cetane number.

The method is characterized in that the cooling fluid 108 can be produced in one or several reactors 10 on board of a vehicle 60 and can be intermediately stored in a tank 61 of the vehicle 60. All embodiments of the invention can be used in a vehicle 60. When using the method in the vehicle 60, micro-reactors 10 and/or micro-catalysts are preferably used for the synthesis of the cooling fluid 108. These micro-reactors 10 and/or micro-catalysts are preferably thermally coupled with the internal combustion engine 62 (e.g. the ship's diesel) in such a way that waste heat (if required) is transferred from the internal combustion engine 62 to the micro-reactors 10 and/or micro-catalysts. In accordance with the invention, so-called small-size chemical circuits can be realized in a vehicle 60 which use $CO_2$ from exhaust gases with locally provided energy (exhaust heat, wind or solar power, flow energy from water flow) in order to provide the cooling fluid 108.

Figure 6:
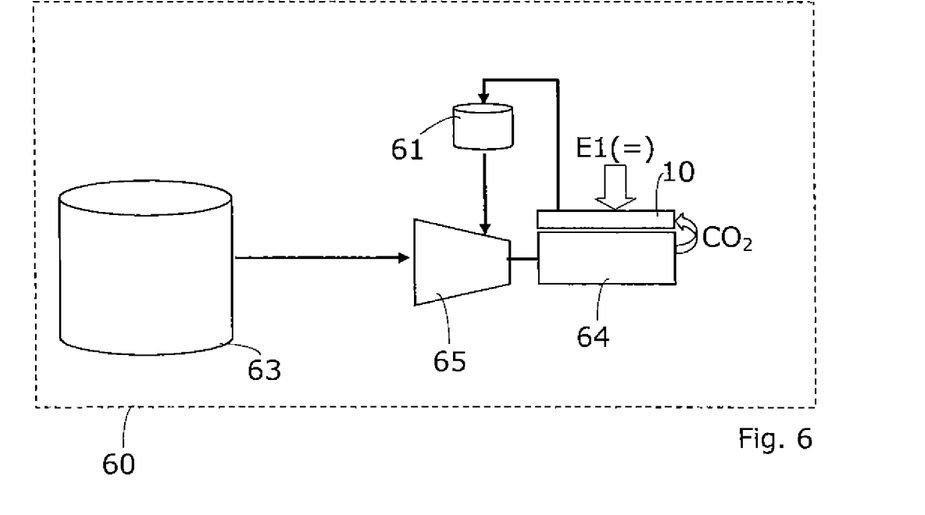
FIG. 6 shows a schematic view of an apparatus which comprises a compressor, a heat conversion installation, two tanks and a microreactor.

FIG. 6 shows a schematic view of an apparatus which is part of a vehicle 60 for example and which in the illustrated example comprises a compressor 65, a heat conversion installation 64 and a micro-reactor 10. Primary fuel (e.g. diesel fuel for ships) is supplied from a tank 63 to the heat conversion installation 64. $CO_2$ exhaust gases (shown here as an arrow) are introduced from the heat conversion installation 64 into a micro-reactor 10. The hydrogen gas is converted there in a catalytic manner with the $CO_2$ into the cooling fluid 108. The hydrogen gas can be produced by supplying DC energy E1. The mixture 108 reaches the tank 61. The cooling fluid 108 is taken from there and used before or in a compressor 65 for example for intake or intermediate cooling, as described above.

The intake cooling and the intermediate cooling are achieved here advantageously by introducing a cooling fluid (alcohol-water mixture 108) into the air or the fuel-air mixture with subsequent evaporation, by means of which the air or fuel-air mixture is cooled by removing the evaporation heat from the cooling fluid. This type of cooling can be realized without any major constructional effort and practically does not lead to any pressure loss. It offers additional advantages in that the cooling is possible far below the ambient temperature and that combustible components of the cooling fluid (alcohol-water mixture 108) will take part in the subsequent combustion and therefore make a respective contribution to the heat supply to the air or fuel-air mixture (working medium). As a result, an alcohol-water mixture 108 can be part of the fuel of diesel engines for example, although such a cooling fluid 108 is otherwise not suitable for diesel engines due to lack of ignition performance (due to inadequate cetane number).

In addition to the ecological effects, the invention also provides sustainable cost benefits.

The method is especially interesting for application segments that are sensitive to the environment such as public transport, logistics businesses, waste-disposal business, agricultural and forestry machines, airports or construction machines in underground mining, and other fields with high sustainability requirements.

A respective compressor unit 65 can be arranged in all embodiments with a gas conducting system or gas line in order to introduce the cooling fluid 108 into the air flow or the fuel-air mixture.

The intake or intermediate cooling with a methanol-water mixture 108 instead of water is especially advantageous because it is less dependent on the humidity content of the intake air.

The method with an alcohol-water mixture 108 as a cooling fluid as described herein is only suitable for gas turbines within limits, in which a part of the compressor air is used as cooling air for the combustion chamber and the turbine part. The possibility of ignition of the alcohol in the gas flow and its consequences need to be taken into account.

| List of reference numerals: | |
| --- | --- |
| Reactor | 10 |
| First upper ring line | 11.1 |
| Second upper ring line | 11.2 |
| Feed lines | 12.1, 12.2 |
| Fluid chamber | 14 |
| Reactor elements | 15.m |
| Fluid supply | 16 |
| Fluid discharge | 17 |
| Reactor tubes | 20.n/20.1-20.3 |
| Gas inlet | 21 |
| Product outlet | 23 |
| Filling opening | 24.1, 24.2 |
| Discharge opening | 25.2, 25.2 |
| Deflection elements | 30.1 and 30.2 |
| Filling station | 50 |
| Refueling process | 51 |
| $CO_2$ withdrawal | 52 |
| Vehicle (e.g. ship) | 60 |
| Second tank | 61 |
| Internal combustion engine | 62 |
| First tank (primary fuel tank) | 63 |
| Heat conversion installation | 64 |
| Compressor (optional) | 65 |
| Silicon-Fire installation | 100 |
| Carbon dioxide | 101 |
| Water | 102 |
| Hydrogen | 103 |
| Provision of carbon dioxide | 104 |
| Performance of electrolysis | 105 |
| Supplying/providing methanol | 107 |
| Transportable cooling fluid (mixture) | 108 |
| (System) control unit | 110 |
| Parameter storage unit | 111 |
| Control or signal lines | 112, 113, 114, 115 |
| Solar thermal installation | 300 |
| Conversion of heat into direct current | 301 |
| Solar installation (photovoltaic system) | 400 |
| Interconnected network | 500 |
| Conversion of alternating voltage into direct current (power supply system) | 501 |
| Silicon-Fire installation | 700 |
| Homogeneously distributed/composed starting material | AS |
| Direct current power | E1 |
| Input quantities | I1, I2, etc. |
| Number of reactor elements | m |
| Number of reactor tubes per reactor element | n |
| Primary power | P1, P2 |

The invention claimed is:

1. A method for providing and using a methanol containing fluid comprising the steps of:
    mixing carbon dioxide gas with hydrogen gas to form a gaseous starting material;
    introducing said starting material into a reactor having a catalyst
    to synthesize by way of catalytic synthesis a methanol fluid containing between 5 and 50% by mass methanol and the remainder water;
    using said methanol fluid for cooling intake air, compressor air, charge air and/or a fuel-air mixture supplied to an internal combustion engine; and,
    after use as a coolant, combusting said methanol fluid with a primary fuel to power said internal combustion engine.

2. The method according to claim 1, wherein said methanol fluid evaporates into a gaseous form when used as a coolant.

3. The method according to claim 1, wherein said methanol fluid comprises less than 30% by mass of methanol and more than 70% by mass of water.

4. The method according to claim 1 wherein water is added to the methanol fluid synthesized by said reactor before it is used for said internal combustion engine.

5. The method according to claim 1, wherein the methanol fluid is stored in a tank after being synthesized in said reactor and before being used as a coolant.

6. The method according to claim 1, wherein the methanol fluid is used for cooling intake air in said internal combustion engine.

7. The method according to claim 1, wherein said methanol fluid is used for cooling a fuel-air mixture supplied to the internal combustion engine.

8. The method according to claim 1, wherein said methanol fluid is used for cooling in a compressor of said internal combustion engine.

9. The method according to claim 1, wherein the carbon dioxide gas used to produce the methanol fluid is generated by said the internal combustion engine.

10. The method according to claim 1, wherein said hydrogen gas is produced directly from water or a water solution.

11. The method according to claim 1, wherein said methanol fluid is stored in a tank of a vehicle.

12. The method according to claim 1, wherein the carbon dioxide is taken from the exhaust gases of a combustion process.

13. The method according to claim 11, wherein the vehicle is:
    a ship;
    a road or off-road vehicle, or
    a an aircraft.

14. The method according to claim 1, wherein said methanol fluid is produced in one or several reactors on board of a vehicle and is intermediately stored in a tank of the vehicle.

\* \* \* \* \*